United States Patent
Cable et al.

(10) Patent No.: US 11,207,227 B1
(45) Date of Patent: *Dec. 28, 2021

(54) HUMAN STABILIZATION PLATFORMS AND RELATED MATTRESSES

(71) Applicant: Cornerstone Research Group, Inc., Miamisburg, OH (US)

(72) Inventors: Kristin M. Cable, Dayton, OH (US); Brian R. Pleiman, Dayton, OH (US); Joshua E. Nieman, Centerville, OH (US)

(73) Assignee: Cornerstone Research Group, Inc., Miamisburg, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/875,745

(22) Filed: May 15, 2020

Related U.S. Application Data (60) Provisional application No. 62/848,459, filed on May 15, 2019.

(51) Int. Cl.
| | |
|---|---|
| *A61G 1/044* | (2006.01) |
| *A61G 1/048* | (2006.01) |
| *A61F 5/37* | (2006.01) |
| *A47C 27/14* | (2006.01) |

(52) U.S. Cl.
CPC .............. *A61G 1/044* (2013.01); *A47C 27/14* (2013.01); *A61F 5/3769* (2013.01); *A61F 5/3776* (2013.01); *A61F 5/3784* (2013.01); *A61G 1/048* (2013.01)

(58) Field of Classification Search
CPC .......... A61G 1/044; A61G 1/048; A61G 1/04; A61F 5/3784; A61F 5/3776; A61F 5/3769; A61F 5/37

USPC ..... 5/628, 625, 621; 128/870, 875, 876, 869
See application file for complete search history.

(56) References Cited

U.S. PATENT DOCUMENTS

| | | | | |
|---|---|---|---|---|
| 3,580,523 | A | * | 5/1971 | Preston ................. A61F 5/3776 297/475 |
| 3,732,863 | A | * | 5/1973 | Harrington ......... A61F 5/05883 602/19 |
| 4,267,830 | A | * | 5/1981 | Vick ..................... A61F 5/3707 128/857 |
| 4,506,664 | A | * | 3/1985 | Brault ................. A61F 5/05883 5/628 |

(Continued)

FOREIGN PATENT DOCUMENTS

WO 2006/134363 A2 12/2006

*Primary Examiner* — Robert G Santos
(74) *Attorney, Agent, or Firm* — TraskBritt (57) ABSTRACT

Mattresses for human stabilization may include a mass of foam material. A cover including a fabric material may at least partially surrounding the mass of foam material. Head blocks including a foam material may be located proximate to one end of the mattress. The fabric material of the cover may at least partially cover the head blocks, and the head blocks may be foldable relative to the mass of foam material to enable the head blocks to be positioned against lateral sides of a person's head. Human stabilization platforms may include a litter having a surface sized and shaped to support a person thereabove. Straps may be configured to restrain a person's head, the straps having releasable connectors at ends thereof. A track may be located on the surface of the litter, and may be configured to receive the connectors to affix the straps to the litter.

18 Claims, 6 Drawing Sheets

(56) References Cited

U.S. PATENT DOCUMENTS

| | | | |
|---|---|---|---|
| 5,865,780 A * | 2/1999 | Tuite | A61F 5/058 |
| | | | 602/32 |
| 6,135,114 A * | 10/2000 | Elliott | A61F 5/3784 |
| | | | 128/869 |
| 6,170,486 B1 | 1/2001 | Islava | |
| 6,363,936 B1 * | 4/2002 | McCormick | A61G 1/044 |
| | | | 128/870 |
| 7,082,632 B2 * | 8/2006 | Hood | A61F 5/05 |
| | | | 5/625 |
| 8,141,555 B1 | 3/2012 | Neusch et al. | |
| 8,584,280 B2 | 11/2013 | Shah | |
| 9,522,078 B2 * | 12/2016 | Pizzini | A61F 5/3776 |
| 10,583,055 B2 * | 3/2020 | Cable | A61G 1/04 |
| 11,071,663 B1 * | 7/2021 | Cable | A61G 1/048 |
| 2004/0016057 A1 | 1/2004 | Traut et al. | |
| 2004/0128767 A1 * | 7/2004 | Hood | A61F 5/05 |
| | | | 5/628 |
| 2004/0244114 A1 | 12/2004 | Robinette | |
| 2005/0229313 A1 | 10/2005 | Tomcany et al. | |
| 2005/0241068 A1 | 11/2005 | Tomcany et al. | |
| 2006/0225213 A1 | 10/2006 | Tomcany | |
| 2010/0288286 A1 * | 11/2010 | Pizzini | A61F 5/3776 |
| | | | 128/845 |
| 2017/0065108 A1 | 3/2017 | Thorn | |
| 2017/0112693 A1 * | 4/2017 | Cable | A61G 1/04 |
| 2020/0360203 A1 * | 11/2020 | Cable | A61G 1/044 |

* cited by examiner

HUMAN STABILIZATION PLATFORMS AND RELATED MATTRESSES

CROSS-REFERENCE TO RELATED APPLICATION

This application claims the benefit under 35 U.S.C. § 119(e) of the priority date of U.S. Provisional Patent Application Ser. No. 62/848,459, filed May 15, 2019, the disclosure of which is hereby incorporated herein in its entirety by this reference.

STATEMENT REGARDING FEDERALLY SPONSORED RESEARCH OR DEVELOPMENT

The subject matter of this disclosure was made with U.S. Government support under Contract Number FA8650-19-C-6918 awarded by the U.S. Air Force Materiel Command, and Contract Numbers W81XWH-10-C-0193, W81XWH-15-C-0050, awarded by the U.S. Army Medical Research Acquisition Activity, to Cornerstone Research Group Inc. The U.S. Government has certain rights in the claimed invention.

TECHNICAL FIELD

This disclosure relates generally to human stabilization platforms to support and substantially immobilize the spine of a person. More specifically, disclosed embodiments relate to human stabilization platforms that may render immobilizing and carrying a person easier, may accommodate the selective attachment of a restraint system at various points along the longitudinal length of the platform to enable deployment of the restraints in a wider variety of configurations, and may reduce the risk of injury during transfers.

BACKGROUND

When a person suffers a head or spinal injury, their head and neck may be immobilized to reduce the risk of further injury during transport and treatment. For example, neck braces, backboards, and crown-encircling stabilizers (also known in the art as "halo" devices) may be used to support a person's head and neck to reduce the risk of further injury.

People who experience traumatic injuries in most cases must, of necessity, endure potentially damaging acceleration, impact and vibrational forces experienced during handling and movement by, for example, search and rescue and emergency medical personnel during transport from an injury site to medical facilities with treatment capabilities. This transport may involve both ground transport and flight on rotary and/or fixed-wing aircraft, all of which may expose the injured person to additional, potentially injurious forces, which may exacerbate the severity of the initial injuries. Proper immobilization and shock load isolation may substantially reduce the mortality and comorbidities associated with these injuries while in transit. Equipment currently used for people with a spinal cord injury (SCI) or traumatic brain injury (TBI) may provide some level of immobilization, but leave substantial room for improvement and flexibility to address specific applications.

BRIEF SUMMARY

Mattresses for human stabilization may include a mass of foam material comprising a surface sized and shaped to support a person thereon. A cover including a fabric material may at least partially surrounding the mass of foam material. Head blocks including the foam material may be located proximate to one end of the mattress. The fabric material of the cover may at least partially cover the head blocks, and the head blocks may be foldable relative to the mass of foam material to enable the head blocks to be positioned against lateral sides of a person's head.

Human stabilization platforms may include a litter having a surface sized and shaped to support a person thereabove. Straps may be configured to restrain a person's head when the person is supported on the litter, the straps having releasable connectors at ends thereof. A track may be located on the surface of the litter. The track may be configured to receive the connectors of the straps to affix the straps to the litter on the surface, and may be located proximate to a longitudinal end of the litter.

Mattresses for human stabilization may include a mass of foam material comprising a surface sized and shaped to support a person thereon. Handles may be located at lateral sides of the mattress, the handles configured to enable the mass of foam material to be lifted without a supporting litter underneath the mass of foam material.

Human stabilization platforms may include a mattress comprising a surface sized and shaped to support a person thereon and a litter sized and shaped to be positioned underneath the mattress. A set of conduits secured to a restraint system may be shaped and configured to overlie the mattress, the set of conduits located to be proximate an arm and shoulder of a person when the person is supported on the mattress and the set of conduits is distributed along a lateral side of the restraint system. A set of rings including connectors may be selectively securable to a track extending along a lateral side of the litter, the set of rings distributed along the track. A strap may be threaded through the set of conduits and the set of rings, a length of the strap threaded through the set of conduits and the set of rings may be adjustable in length to adjust a fit of the restraint system.

BRIEF DESCRIPTION OF THE DRAWINGS

While this disclosure concludes with claims particularly pointing out and distinctly claiming specific embodiments, various features and advantages of embodiments within the scope of this disclosure may be more readily ascertained from the following description when read in conjunction with the accompanying drawings, in which:

DETAILED DESCRIPTION

The illustrations presented in this disclosure are not meant to be actual views of any particular human stabilization platform or component thereof, but are merely idealized representations employed to describe illustrative embodiments. Thus, the drawings are not necessarily to scale.

Figure 2:
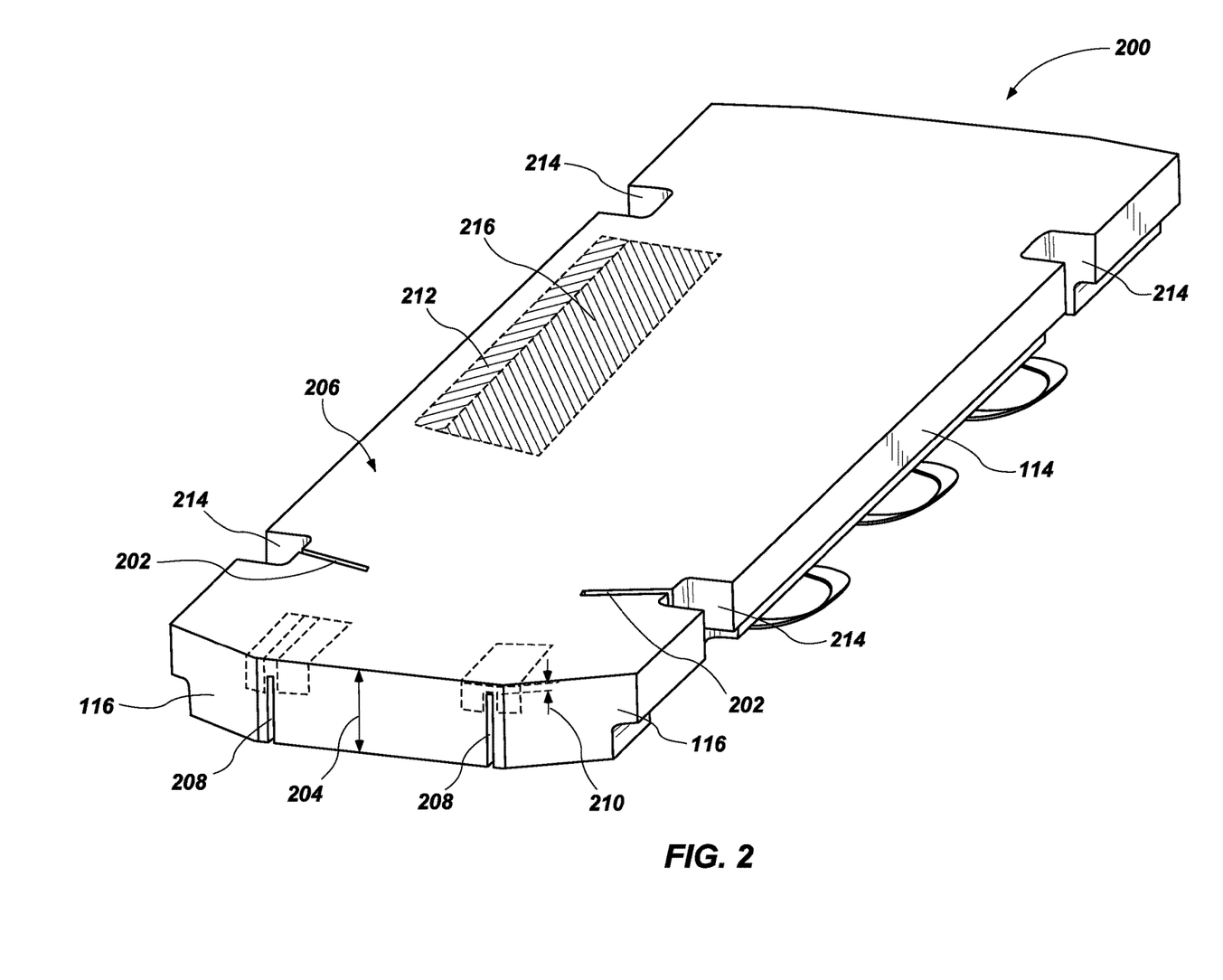
FIG. 2 is a perspective, top view of the mattress of FIG. 1.

As used in this disclosure, the term "longitudinal" means and includes directions extending at least substantially head-to-toe when a person is secured in a human stabilization platform as shown in FIG. 2. The term "lateral," as used in this disclosure, means and includes directions extending at least substantially shoulder-to-shoulder when a person is secured in a human stabilization platform as shown in FIG. 2.

As used herein, the terms "substantially" and "about" in reference to a given parameter, property, or condition means and includes to a degree that one of ordinary skill in the art would understand that the given parameter, property, or condition is met with a degree of variance, such as within acceptable manufacturing tolerances. For example, a parameter that is substantially or about a specified value may be at least about 90% the specified value, at least about 95% the specified value, at least about 99% the specified value, or even at least about 99.9% the specified value.

As used herein, the term "ring" means and includes any structure forming an enclosed region through which a strap of a restraint system may be threaded. For example, rings include eyelets, loops, annuluses, and closed sections of rigid material (e.g., metal) having any cross-sectional shape and forming any peripheral shape (e.g., circular, elliptical, triangular, rectangular).

Existing equipment for immobilizing traumatically injured persons may not be effective to isolate the patient from the dynamic multi-axial shock loading and vibrations present during transport. Treatment efficacy may be further diminished due to the current systems' inability to properly address polytrauma treatment issues, provide clear access to injury sites, manage bodily fluids, reduce the risk of pressure ulcerations, or be applied to an injured person in a variety of positions and orientations. With the increasing prevalence of SCI, TBI, and polytrauma patients due to the expanded use by adversaries of improvised explosive devices (IEDs) on military forces, a renewed transport platform design may improve the specific transport, safety, care, and comfort needs of both the injured and caregivers.

Disclosed embodiments relate generally to human stabilization platforms that may render immobilizing and carrying a person easier, may accommodate the selective attachment of a restraint system at various points along the longitudinal length of the platform to enable deployment of the restraints in a wider variety of configurations, and may reduce the risk of injury during transfers. More specifically, embodiments of this disclosure may relate to embodiments of human stabilization platforms including head blocks that may be easier to put into position to immobilize a person's neck and head, multiple tracks having points of connection distributed along their lengths to provide more flexibility in deploying and positioning restraints, and variations in stiffness of materials in different regions of a mattress, as well as optional handles integrated into the mattress itself, to render manual transport of the human stabilization platform and/or the mattress thereof to a site of use easier, and to provide more support and ease transitions when moving a patient on the mattress without the additional support of a litter or restraint system.

Figure 1:
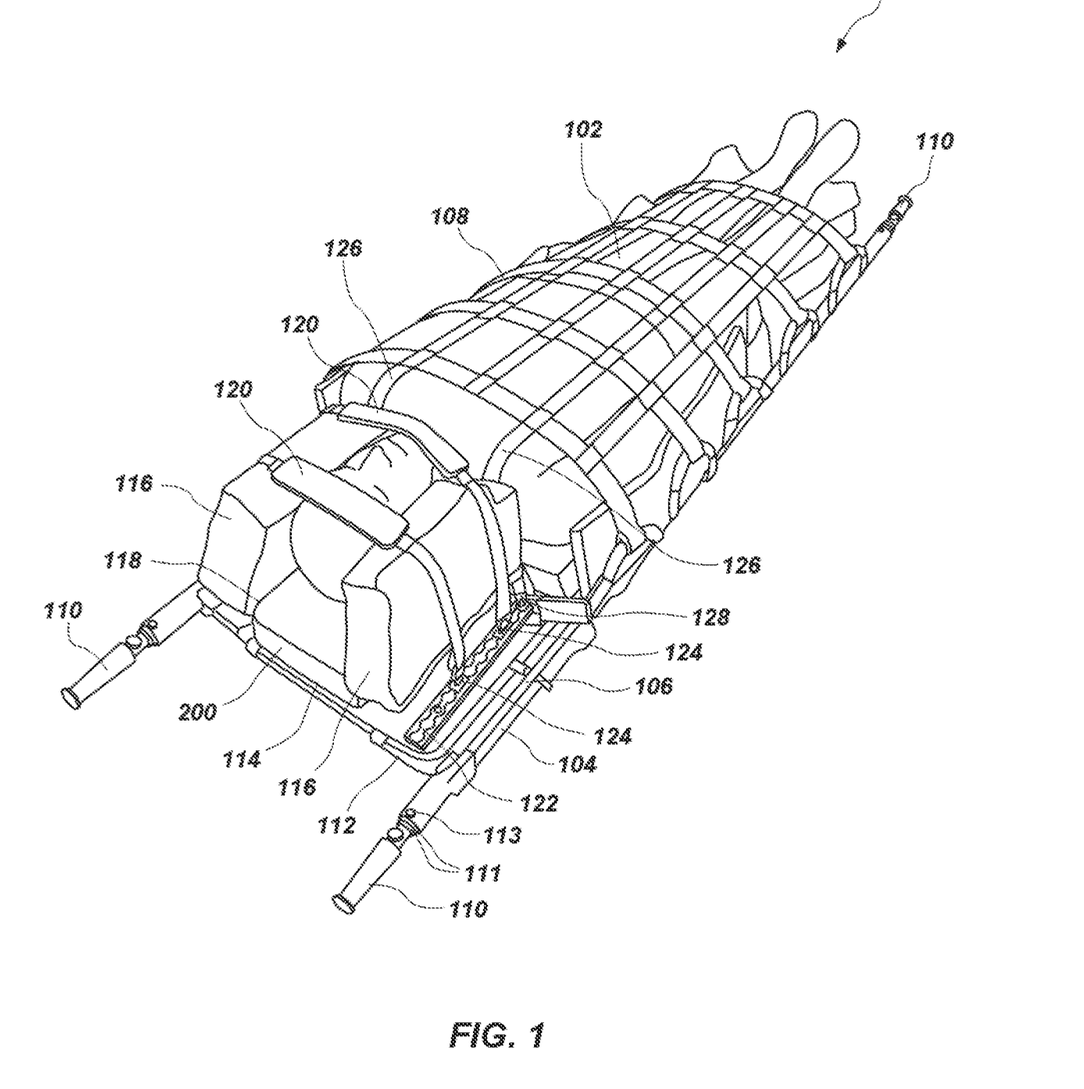
FIG. 1 is a perspective, top view of a human stabilization platform for supporting and at least substantially immobilizing a person during transport and/or treatment.

FIG. 1 is a perspective, top view of a human stabilization platform 100 for supporting and at least substantially immobilizing a person 102 during transport and/or treatment. The human stabilization platform 100 may include, for example, a litter 104 having a surface 106 sized and shaped to support a person 102 thereabove, a mattress 200 sized and shaped to be supported on the surface 106 of the litter 104 and to receive the person 102 thereon, and a restraint system 108 configured to restrain portions of a body of a person 102 and secure the person 102 to the mattress 200 and the litter 104 when the person is supported on the litter.

The surface 106 of the litter 104 may be, for example, an upper surface, which may also be characterized as a major surface, for supporting the mattress 200 and a person 102 on the mattress 200. The litter 104 and the surface 106 thereof may exhibit, for example, an at least substantially rectangular shape. The litter 104 may be a rigid structure configured to at least substantially retain its shape to maintain alignment of the spine of the person 102 spine and reduce the likelihood of further injuring the person 102 when subjected to the accelerations, forces, and vibrations of transport. In some embodiments, the litter 104 may include a composite material. More specifically, the litter 104 may include a honeycomb core and a surrounding fiber-matrix composite material. Such materials may reduce the weight of the litter 104 while maintaining or increasing its rigidity and strength in comparison to conventional litters, while also dampening transmission of potentially harmful vibrations to the person 102. The litter 104 may be configured to support a 95th percentile male person 102 (e.g., a person 102 weighing up to about 250 pounds) and a substantial load (e.g., at least about 75 pounds, such as about 100 pounds or more) of medical equipment through exposure to 8 g of downward or lateral accelerations and 12 g of forward accelerations. A rigidity of the litter 104 and other components of the human stabilization platform 100 may cause a maximum deflection of the human stabilization platform 100 to be, for example, about 2.0 inches or less when subjected to an 8 g downward acceleration, in comparison to when in an unstressed condition.

Handles 110 may be located at each end of the litter 104. Each handle 110 may be adjustable with respect to a remainder of the litter 104. For example, each handle 110 may be rotatable with respect to the litter 104 to facilitate easier handling by another person to carry the human stabilization platform 100 and also facilitate storage of the handles 110. For example, an axis of rotation about which each handle 110 is configured to rotate may extend in a direction at least substantially perpendicular to the surface 106 of the litter 104 to enable the handles 110 to pivot laterally inwardly and outwardly. Each handle 110 may include, for example, a thermoplastic portion sized and shaped to be gripped by a person's hand, a strong hinge (e.g., of high-strength hardened steel) secured to the thermoplastic portion, and an attachment member (e.g., rivets, bolts, screws, adhesive, or any combination of these) securing the hinge to an end of the litter 104.

As another example, each handle 110 may be telescopable with respect to the remainder of the litter 104. More specifically, each handle 110 may be selectively fixable in a retracted position where a given handle 110 is located proximate to the mattress 200, selectively fixable in an extended position where the given handle 110 is located distal from the mattress 200, and selectively movable between the retracted position and the extended position utilizing telescoping members 111 to enable the selective movement of the handle 110. As a specific, nonlimiting example, each handle 110 may be selectively fixable in a retracted position where a given handle 110 is located proximate to the mattress 200 utilizing a fixing device 113 (e.g., a spring-loaded pin, a friction collar), selectively fixable in an extended position where the given handle 110 is located distal from the mattress 200 utilizing the fixing device 113, selectively fixable in any of a variety of intermediate locations between the retracted and extended positions, and selectively movable between the retracted position, the intermediate locations, and the extended position utilizing the telescoping members 111 to enable the selective movement of the handle 110.

The litter 104 may include a gatch 112 located to receive a person's head and back thereabove. The gatch 112 may include a rotatably liftable backrest and an adjustable lifting mechanism. The backrest may be further secured to the support structure by a hinge located at an end of the backrest positioned to be located proximate a person's waist when the person is supported on the litter 104. The adjustable lifting mechanism may secure the backrest to a remainder of the litter 104, and may be selectably extendable and securable in position to enable the backrest to rotate about an axis extending laterally across and parallel to the surface 106 of the litter 104, and to be secured in place to stabilize a person's torso at a desired angle relative to the surface 106 of the litter 104. The adjustable lifting mechanism may include, for example, a telescoping member on each lateral side of the litter 104 having one end secured to, and rotatable with respect to, the middle of a longitudinal extent thereof) and another, opposite end secured, and rotatable with respect to, a remainder of the litter 104. The telescoping members may be securable at any of a variety of selected lengths to enable the backrest to be secured in position at various angles relative to the remainder of the litter 104. Suitable telescoping members include, for example, telescoping gas spring mechanisms commercially available from Camloc Motion Control and distributed by Arconic Fastening Systems & Rings of 3990 Heritage Oak Ct., Simi Valley, Calif. 93063.

The mattress 200 may be sized and shaped to be supported on, and optionally secured to, the surface 106 of the litter 104. A material of the mattress 200 may be configured to distribute pressure across an area of a person's body, reducing peak pressure on any given body area and reducing the risk of pressure ulcers. The mattress 200 may further include, for example, a cover 114 of a fabric material sized and shaped to at least partially surround the foam material.

The human stabilization platform 100 may include two head blocks 116 for positioning on each lateral side of the mattress 200 proximate to one longitudinal end to flank the head of the person 102. The head blocks 116 may include, for example, masses of foam material that may be movable relative to a remainder of the mattress 200.

In some embodiments, the foam material of the head blocks 116 may be, for example, contiguous with, and unitary and integral to, the foam material of a remainder of the mattress 200. More specifically, an entirety of the foam material of the head blocks 116 and the remainder of the mattress 200 may be formed in a single molding and/or curing process. In such embodiments, the portions of foam material extending between the head blocks 116 and the remainder of the mattress 200 may have a smaller thickness than thicknesses of the head blocks 116 and/or the remainder of the mattress 200 themselves, as measured in a direction perpendicular to the surface 106 of the litter 104. With such a variation in thickness, the head blocks 116 may be rotatable relative to the remainder of the mattress 200, about an axis oriented generally in a head-to-foot direction longitudinally along the litter 104 when a person is supported on the human stabilization platform 100.

In other embodiments, the foam material of the head blocks 116 may be discontinuous, and distinct, from the foam material of the remainder of the mattress 200. For example, the fabric material of the cover 114 may extend continuously from locations covering the foam material of the remainder of the mattress 200 to locations covering the foam material of the head blocks 116, with a seam 118 of the cover 114 laterally interposed between those portions of the cover 114 at least partially surrounding each of the head blocks 116 and those portions of the cover 114 at least partially surrounding the remainder of the mattress 200. With such a seam 118, each head block 116 may be rotatable relative to the remainder of the mattress 200, about an axis oriented generally in a head-to-foot direction longitudinally along the litter 104 when a person is supported on the human stabilization platform 100. As another example, the head blocks 116 may be entirely separate from a remainder of the mattress 200, such that each head block 116 may include its own dedicated cover 114 separate and distinct from the cover 114 at least partially surrounding the remainder of the mattress 200. In such embodiments, the head blocks 116 may be selectively securable in position relative to the remainder of the mattress 200, such as, for example, at least partially utilizing hook and loop attachments on the head blocks 116 and on the lateral sides of the portion of the mattress 200 on which a person's head is to be supported.

The head blocks 116 may be securable against the person's head to help reduce head motion during transport at least partially utilizing straps 120 extending from one lateral side of the litter 104, over the head blocks 116, back to the litter 104 on another, opposite lateral side thereof. For example, the litter 104 may include points of attachment on the surface 106 of the litter 104 to which ends of the straps 120 may be selectively secured to restrain the head of the person 102 and to urge the head blocks 116 against the lateral sides of the head of the person 102. The ends of the straps 120 may also be selectively released from the points of attachment to release the head of the person 102 and free the head blocks 116 from contact with the head of the person 102. In some embodiments, the points of attachment may be in the form of two first tracks 122, each on a different lateral side of the litter 104 and proximate to a longitudinal end thereof. Each first track 122 may have a series of points of attachment distributed along a longitudinal length of the respective first track 122. The distal ends of each strap 120 may include connectors 124 configured to be selectively secured to respective points of attachment along the first track 122. For example, one strap 120 may have the connectors 124 at its distal ends selectively secured to the first tracks 122 proximate to the distal end of the litter 104, enabling the strap 120 to extend over and secure the forehead of the person 102. Another strap 120 may have the connector 124 at its distal ends selectively secured to the first tracks 122 at a location on the first tracks 122 distal from the longitudinal end of the litter 104, enabling the other strap 120 to extend across and secure the chin of the person 102. Additional detail regarding the structure of the connectors 124 and the first tracks 122 is provided in connection with FIG. 4 through FIG. 7.

In embodiments where the head blocks 116 are secured, and foldable relative, to the remainder of the mattress 200, the head blocks 116 may selectively conceal and/or reveal the first track 122 depending on the positions of the head blocks 116. For example, a respective first track 122 may be covered by its associated head block 116 when the head block 116 is in an unfolded state, lying against the surface 106 of the litter 104. When the head block 116 is placed in a folded state, such as, for example, by rotating the head block 116 upward away from the surface 106 and laterally inward toward the head of the person 102, the first track 122 may be exposed for receiving the connectors 124 of the straps 120 and/or the connectors 124 of the shoulder straps 126 of the restraint system 108. The connectors 124 at ends of the straps 120 and associated first tracks 122 may be configured, for example, in a manner similar to other connectors and tracks of the human stabilization platform 100 shown and described in greater detail in connection with FIGS. 4 through 7.

The restraint system 108 may include, for example, a five-point harness, a pair of wrist-restraint straps, an adjustable pelvic-restraint strap, a pair of thigh-restraint straps, a pair of ankle-restraint straps, or any combination or subcombination of these. Components of the restraint system 108 may be securable to the litter 104 and positioned to secure a person 102 to the human stabilization platform 100. One or more of the foregoing components of the restraint system 108 may be adjustable, which may accommodate people of a wider variety of body sizes and shapes and may enable a person 102 to be secured to the human stabilization platform 100 while reducing (e.g., eliminating) contact between the restraint system 108 and any injury sites. In some embodiments, the restraint system 108 may include a 6-point harness configuration including two shoulder straps 126 attached to the backrest of the litter 104, such as, for example, utilizing connectors 128 selectively securable to a respective first track 122, enabling elevation of the head and back of the person 102 in either a restrained, or unrestrained, state. In other embodiments, the restraint system 108 may also include a lattice harness configuration with an evenly spaced, "net" style restraint still including at least two shoulder straps 126 securable to the backrest of the litter 104, such as, for example, utilizing connectors 128 selectively securable to a respective first track 122. Any remaining straps of the restraint system 108, such as those that may remain in embodiments where the restraint system 108 is configured as a net style restraint, may be securable to the rail 412 (see FIG. 4-6) on a lateral side of the litter 104, as described in greater detail in connection with FIGS. 4 through 7.

FIG. 2 is a perspective, top view of the mattress 200 of FIG. 1. The mattress 200 may include, for example, slots, slits, grooves, channels, holes, or other passages therethrough to enable straps of the restraint system 108 to extend from below the mattress 200 proximate the litter 104, across a thickness 204 of the mattress 200, to above the mattress 200 on a side of the mattress 200 opposite the litter 104 (see FIG. 1). For example, the mattress 200 may include at least two shoulder slots 202 configured to accommodate the shoulder straps 126 (see FIG. 1) and enable the connectors 128 (see FIG. 1) associated therewith to pass from over a major surface 206 of the mattress 200 sized and shaped to support a person 102 (see FIG. 1) thereon, across a thickness 204 of the mattress 200, to the litter 104 (see FIG. 1). Each shoulder slot 202 may extend, for example, from a lateral periphery of the mattress 200 laterally inward to a location above where shoulders of a person 102 are configured to be received and proximate to where the neck of the person 102 is to be received. The shoulder slots 202 may extend entirely through the thickness 204 of the mattress 200, forming a discontinuity between the foam material of the head blocks 116 and the foam material of the remainder of the mattress 200.

The mattress 200 may further include block slots 208 proximate to a lateral boundary between the head blocks 116 and the remainder of the mattress 200, and optionally configured to enable the head blocks 116 to move relative to the remainder of the mattress 200. For example, the block slots 208 may extend from a longitudinal periphery of the mattress 200 proximate to where a top of a head of the person 102 is to be received, longitudinally downward along a position on the mattress 200 proximate to where the person's head and neck are to be received, to intersect with the shoulder slots 202. In some embodiments, the block slots 208 may extend only partially through the thickness 210 of the mattress 200. For example, the thickness 210 of the mattress 200 along and within the block slots 208, as measured in a direction perpendicular to the major surface 206 of the mattress 200 may be less than the thickness 204 of the remainder of the mattress 200, such as, for example, along and within those portions of the mattress 200 for directly underlying the head of a person 102 (see FIG. 1). More specifically, the thickness 210 of the mattress 200 within the block slots 208 may be, for example, between about 0.1% and about 10% of the maximum thickness 204 of the remainder of the mattress 200. As a specific, nonlimiting example, the thickness 210 of the mattress 200 within the block slots 208 may be between about 1% and about 5% (e.g., about 2.5%) of the maximum thickness 204 of the remainder of the mattress 200.

In embodiments where the foam material 212 of the head blocks 116 is contiguous with the foam material 212 of the remainder of the mattress 200, as reflected in the cutout section on the right-hand side of FIG. 2, the differences in thickness between those portions of the foam material 212 overlying the block slots 208 and those portions of the foam material 212 at a maximum thickness may be at least substantially the same as those differences in thickness 204, 210 described above in connection with the mattress 200 itself. In embodiments wherein the foam material 212 of the head blocks 116 is discontinuous from the foam material 212 of the remainder of the mattress 200, the differences in thickness 204, 210 between the those portions of the mattress 200 overlying the block slots 208 and those portions of the mattress 200 at the maximum thickness 204 may be maintained by, for example, the shape of the cover 114 (e.g., the inclusion of a seam 118 laterally interposed between each head block 116 and the portion of the mattress 200 for receiving the head of a person 102 (see FIG. 1) thereon), as shown in the cutout section on the left-hand side of FIG. 2.

In some embodiments, the mattress 200 may include cut-out slots 214 proximate to positions on the major surface 206 for receiving the shoulders, head, and lower legs of a person 102 (see FIG. 1). The cut-out slots 214 may be configured to enable additional straps of the restraint system 108 to pass from over the major surface 206 of the mattress 200, across the thickness 204 of the mattress 200, to the litter 104 (see FIG. 1). The cut-out slot 214 may also accommodate feet 418 (see FIG. 4) secured to an overlying human stabilization platform 100 to enable easier stacking of human stabilization platforms 100 for storage and bulk transport when not in use. The cut-out slot 214 may extend, for example, from the lateral periphery of the mattress 200, laterally inward, and may extend entirely through the thickness 204 of the mattress 200 to form a void having an at least substantially polygonal (e.g., rectangular) shape.

In some embodiments, mattresses in accordance with this disclosure may include additional slots, slits, grooves, channels, holes, or other passages therethrough in locations other than those explicitly shown and described in connection with FIGS. 1 and 2 to enable straps of the restraint system 108 (see FIG. 1) to extend from below the mattress 200 proximate the litter 104, across a thickness of the mattress 200, to above the mattress 200 on a side of the mattress 200 opposite the litter 104 (see FIG. 1).

The mattress 200 may also incorporate stiffer foam material 212 along the periphery of the mattress than softer, more compliant foam material 216 located inward centrally with respect to the periphery to better support and maintain position and alignment of a person 102 (see FIG. 1) on the major surface 206 of the mattress 200. For example, the foam material 212 of the mattress 200 running longitudinally from a location where the feet of the person 102 (see FIG. 1) are to be received to a location where the head of the person 102 (see FIG. 1) is to be received, and concentrated at and proximate to the lateral sides of the mattress 200, may be stiffer than the foam material 216 located laterally inward from the lateral periphery of the mattress 200. In some embodiments, the stiffer foam material 212 may also be located within the portion of the mattress 200 positioned to directly underlie the head of the person 102 (see FIG. 1), which may also be characterized as a "pillow." More specifically, a maximum deflection of the foam material 212 located proximate to one or more peripheral regions of the mattress 200 may be about 75% or less of a maximum deflection of the foam material 216 located distal from the relevant peripheral regions of the mattress 200 under the same load. As a specific, nonlimiting example, the maximum deflection of the foam material 212 located proximate to the lateral periphery and one longitudinal periphery (i.e., the pillow) of the mattress 200 may be about 50% or less (e.g., about 35%) of the maximum deflection of the foam material 216 located distal from the relevant peripheral regions of the mattress 200 under the same load. Such relative differences in stiffness for the foam materials 212, 216 of the mattress 200 in the disclosed regions may be particularly useful for maintaining adequate support and positioning when transferring a person 102 (see FIG. 1) supported on the mattress 200 between different litters 104. The stiffer foam material 212 may also help to reduce torso lateral motion of the person 102 (see FIG. 1) during vehicular transport.

Figure 3:
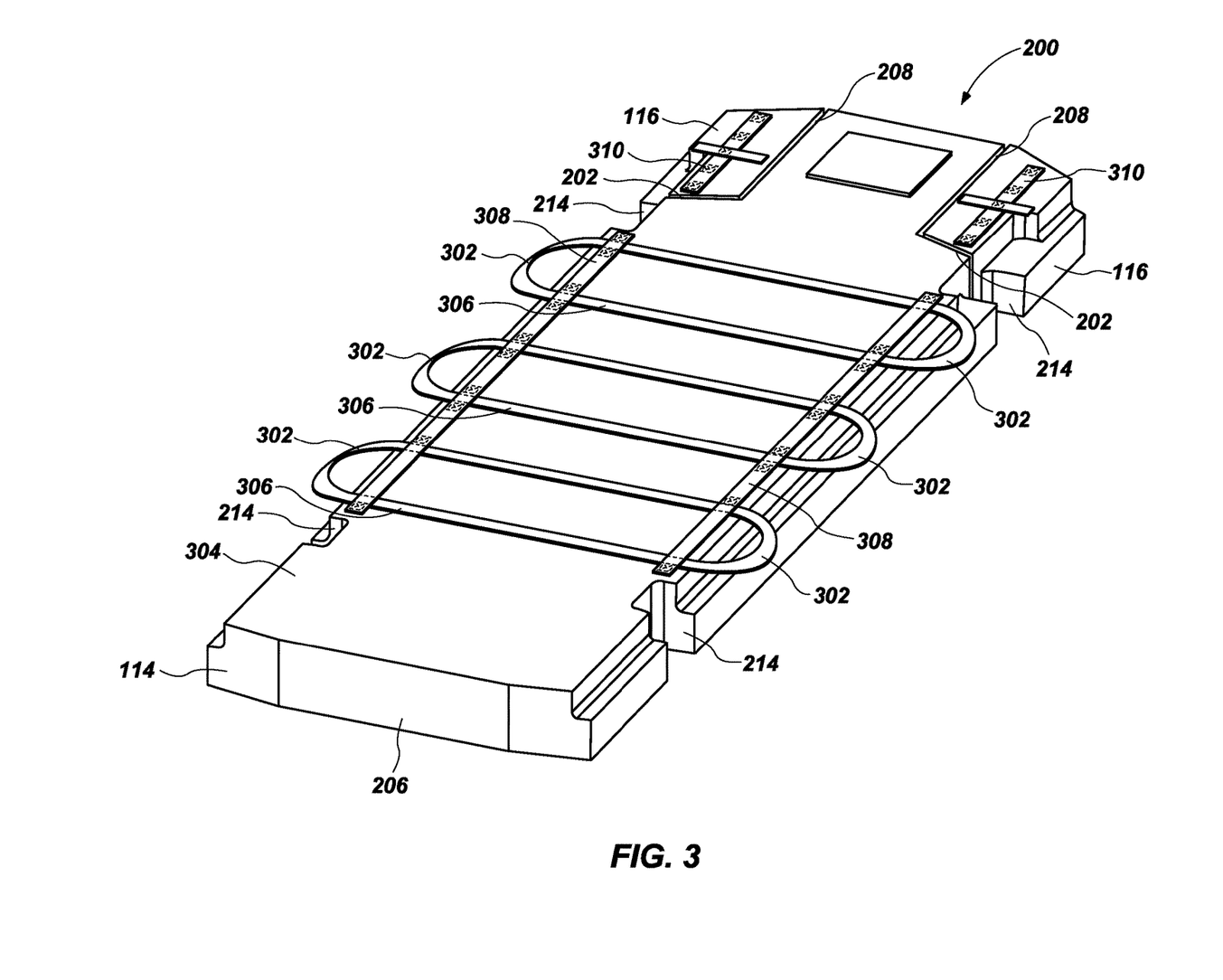
FIG. 3 is a perspective, bottom view of the mattress of FIG. 2.

FIG. 3 is a perspective, underside view of the mattress 200 of FIG. 2. The mattress 200 may include lifting handles 302 for facilitating transfer and movement of the mattress 200 itself. The lifting handles 302 may extend laterally outward from, and be secured to, another major surface 304 of the mattress 200 located on a side of the mattress 200 opposite the first major surface 206 on which a person 102 (see FIG. 1) is to be supported. More specifically, points of connection between the lifting handles 302 and the cover 114 may be located proximate to the lateral sides of the cover 114, and portions of the lifting handles 302 may extend laterally beyond the lateral sides of the cover 114 for grasping. As a specific, nonlimiting example, the lifting handle 302 may include closed rings 306 of woven polymer fabric material, each ring 306 forming an at least substantially obround shape, with portions of the rings 306 underlying and extending laterally across the other major surface 304 and remainders of the rings 306 forming looped lifting handles 302 extending laterally beyond the lateral side surfaces of the mattress 200.

The use of softer foam material proximate to the lateral center, and stiffer foam material along the lateral sides of the mattress 200, combined with the use of lifting handles 302 proximate to the lateral sides, enables the mattress 200 to roll up and conform to a person 102 (see FIG. 1) supported on the mattress 200. For example, when a person 102 is supported on the mattress 200 and the mattress 200 is lifted without the support of the litter 104 (see FIG. 1) utilizing the lifting handles 302, the lateral sides of the mattress 200 may curl upward and laterally inward toward the person 102, and the mattress 200 may inhibit deformation that would produce bending at the waist of the person 102 waist and along the spine of the person 102 spine. As a result, the mattress 200 may better support the person 102 (see FIG. 1) in terms of stability and avoidance of bending and torsional stresses during transfer between different litters 104 (see FIG. 1) and may reduce (e.g., minimize) independent body motion of the person 102 even without the benefit of the restraint system 108 (see FIG. 1).

In some embodiments, the mattress 200 may include one or more reinforcement straps 308 configured to reinforce the lifting handles 302 and/or the lateral sides of the mattress 200. For example, each reinforcement strap 308 may be located proximate to a given lateral side of the mattress 200 and extend longitudinally between locations proximate to the cut-out slots 214. More specifically, the reinforcement straps 308 may include strips of woven polymer fabric material sewn to the cover 114 at the same points of connection as the lifting handles 302.

In some embodiments, the mattress 200 may include one or more securing straps 310 configured to better secure the straps 120 (see FIG. 1) for restraining the head of the person 102 (see FIG. 1) head and urging the head blocks 116 against the lateral sides of the head of the person 102 (see FIG. 1) head. For example, each securing strap 310 may be located proximate to a given lateral side of the associated head block 116 and extend longitudinally between a location proximate to the longitudinal end of the mattress 200 and another location proximate to the associated shoulder slot 202. More specifically, the securing straps 310 may include strips of woven polymer fabric material sewn to the cover 114 at discrete points of connection, such that the straps 120 may be threaded through the securing straps 310 to better secure the head blocks 116 in place.

Figure 4:
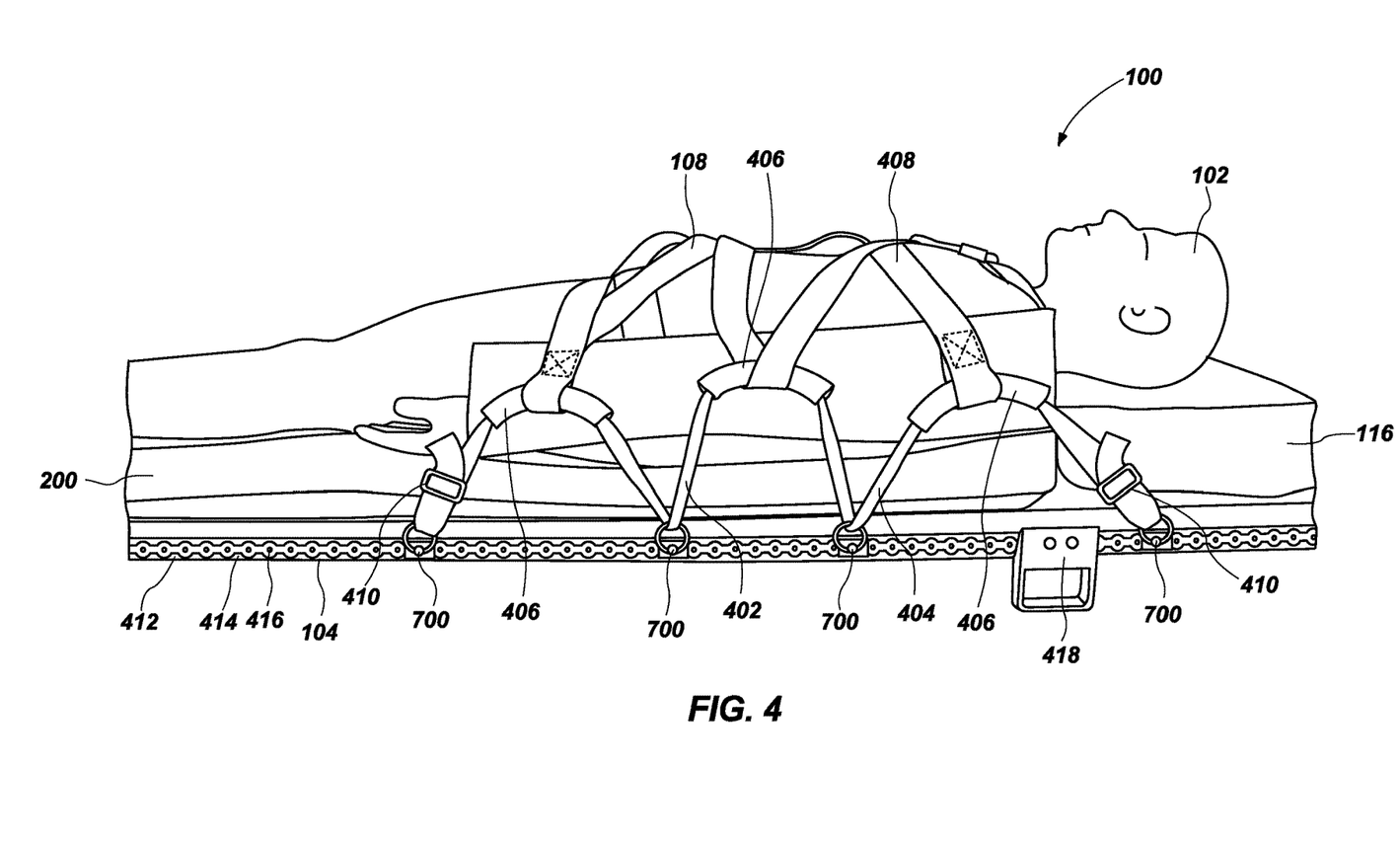
FIG. 4 is a side view of the human stabilization platform of FIG. 1.

FIG. 4 is a side view of the human stabilization platform 100 of FIG. 1. In some embodiments, the restraint system 108 may include a "shoelace" style interfacing mechanism 402, including one or more straps 404 (e.g., lengths of webbing) extending through alternating lacing conduits 406 (e.g., eyelets, loops, sleeves, carabiners) securable to a remainder of the restraint system 108 and rings 700 (e.g., eyelets, loops, sleeves, carabiners) securable to the litter 104. For example, the lacing conduits 406 may extend along, and be secured to, the lateral sides of the restraint system 108 in a position overlying the litter 104 and optionally the mattress 200 proximate to the shoulders, arms, and wrists of a person 102 when the restraint system 108 is in position over the person's body. Continuing the example, the rings 700 may extend along, and be secured to, the lateral sides of the litter 104, and a respective strap 404 may be threaded through alternating ones of the rings 700 and the lacing conduits 406 on each lateral side of the human stabilization platform 100 such that the interfacing mechanism 402 extends between, and is secured to each of, the restraint system 108 and the litter 104. The lacing conduits 406 may alternate with the rings 700 along the lateral sides of the restraint system 108 and the litter 104, such that a lacing conduit 406 is located longitudinally between each pair of rings 700 and a ring 700 is located longitudinally between each pair of lacing conduits 406.

The length of the straps 404 that thread through the lacing conduits 406 and the rings 700 may be adjustable, enabling the interfacing mechanism 402 to adjust the fit of the restraint system 108 independent of the straps 408 of the restraint system 108 itself. For example, the straps 404 may include selectable buckles 410 (e.g., clamps, ratchets, friction slides) proximate to the distal ends of each strap 404, which may selectively release the strap 404 to pull the length of the strap 404 through the buckle 410 to tighten or loosen the strap 404 and selectively fix the strap 404 in place to inhibit changing the length of the strap 404 that threads through the lacing conduits 406 and the rings 700. As a specific, nonlimiting example, the straps 404 and associated buckles 410 may include ratcheting straps commercially available from Ancra Cargo of 2685 Circleport Dr., Erlanger, Ky. 41018. Interlacing of the straps 404 through the rings 700 and the lacing conduits 406 may enable changes in length for the straps 404 to draw the restraint system 108 closer to the litter 104, or release the lateral sides of the restraint system 108 to move farther from the litter 104. The restraint system 108 with the interfacing mechanism 402 may be tightened in some embodiments by pulling on two webbing loops on each distal end of the strap 404, reducing (e.g., minimizing) the time required to install and adjust the fit of the restraint system 108 while reducing (e.g., minimizing) motion of the person 102 during transport.

Figure 5:
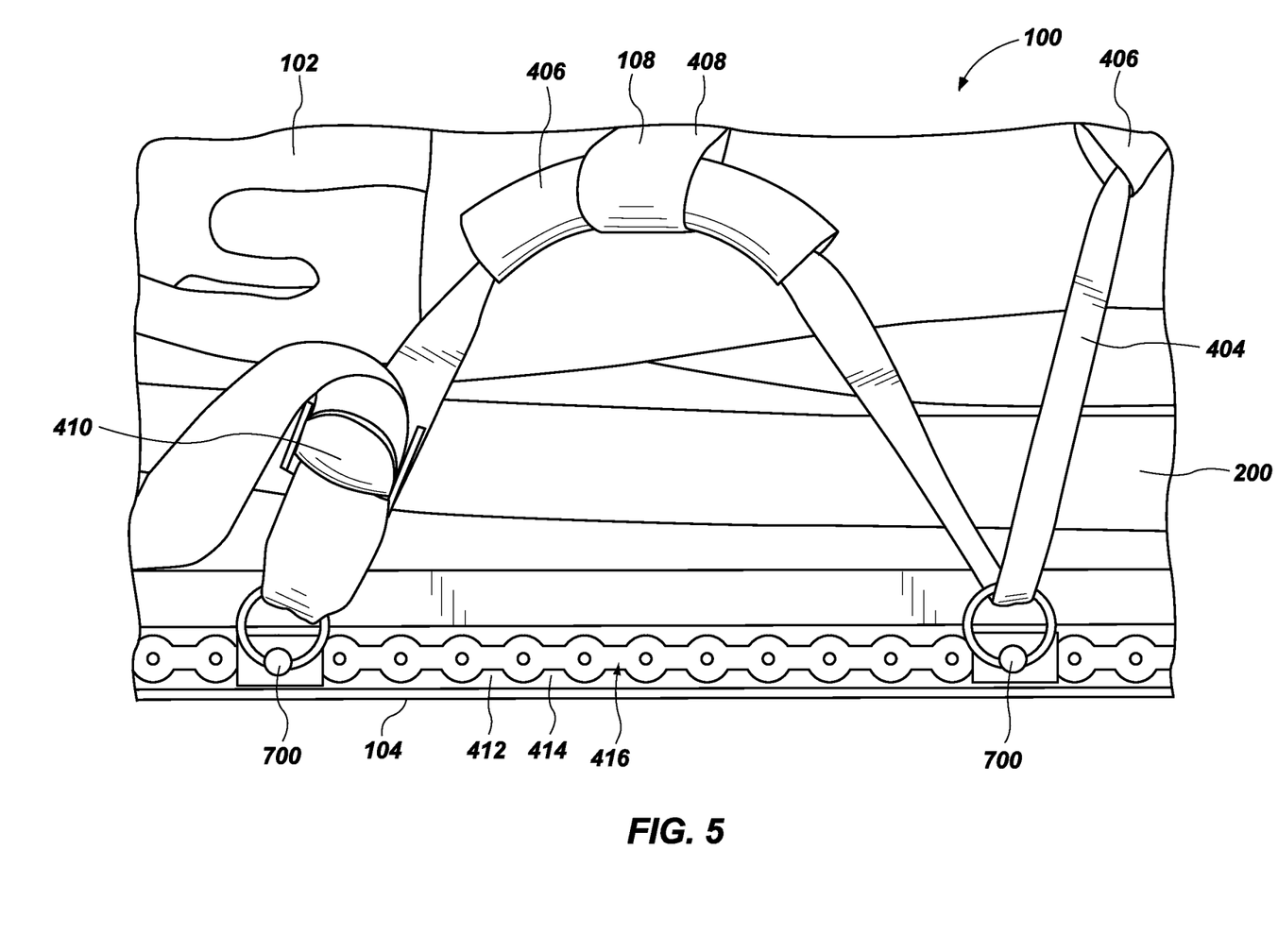
FIG. 5 is an enlarged side view of a portion of the human stabilization platform of FIG. 4.

FIG. 5 is an enlarged side view of a portion of the human stabilization platform 100 of FIG. 4. The lacing conduits 406 may include, for example, tubular sections of resilient material sized and shaped for the straps 404 of the interfacing mechanism 402 to extend therethrough, positioned for the straps 408 of the restraint system 108 to be secured thereto (e.g., by wrapping around the lacing conduits 406, being sewn to the lacing conduits 406), and for a human hand to grasp at least substantially comfortably. More specifically, the lacing conduits 406 may include tubes of rubber and/or resilient polymer material between about 4 inches and about 12 inches in length and between about 0.5 inch and about 2 inches in diameter.

Referring collectively to FIGS. 4 and 5, a rail 412 may extend longitudinally from proximate a portion of the litter 104 configured to underlie the head of the person 102 to proximate a portion of the litter 104 configured to underlie the lower legs of the person 102 lower legs and feet on each lateral side of the litter 104. Each rail 412 may include, for example, a rigid beam extending along the lateral side of the litter 104, and may include a second track 414 extending along at least a portion of the longitudinal length of the respective rail 412. Each second track 414 may include selectable connectors 416 (which may also be characterized as "receiving sites" or "anchoring sites") distributed along at least a portion of the longitudinal length of the respective second track 414 and rail 412. For example, the connectors 416 may be distributed along at least 50% of the longitudinal length of each rail 412. More specifically, the connectors 416 may be distributed along at least 75% (e.g., at least 90%) of the longitudinal length of each rail 412.

The connectors 416 may be configured to receive the rings 700 of the interfacing mechanism 402 and other modular accessories to be secured to the human stabilization platform 100. For example, the connectors 416 may include, for example, a series of holes or slots extending through at least portions of each second track 414, such that modular accessories may be secured to, and distributed along, the second track 414 by pins, hooks, loops, clamps, or threaded members extending at least partially through the holes, which may optionally be threaded themselves. Other modular accessories suitable for selective attachment to the selectable attachment structures may include, for example, a handle, a vibration-damping foot 418 configured to rest, and support the human stabilization platform 100, on an underlying surface, and a fluid management system sized and shaped to extend from one associated selectable attachment structure on one lateral side of the support structure, over the support structure, to another associated selectable attachment structure on an opposite lateral side of the support structure.

Figure 6:
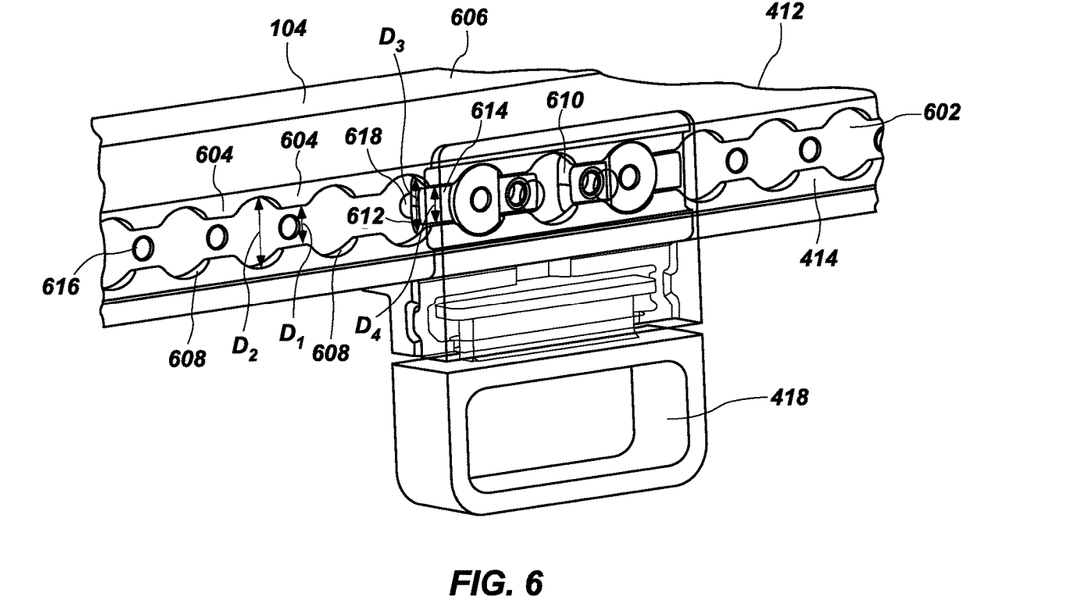
FIG. 6 is an enlarged, perspective, partially transparent, side view of an active connection between a foot and connectors of a second track of the human stabilization platform of FIG. 4.

FIG. 6 is an enlarged, perspective, partially transparent, side view of an active connection between one of the feet 418 and the connectors 416 of the second track 414 of the human stabilization platform 100 of FIG. 4. The connectors 416 of the second track 414 may include and/or be formed from, for example, a channel 602 having an at least substantially "C" shaped cross section (e.g., a rectangle missing a portion of one side of the rectangle) and having alternating teeth 604 spaced from one another by a first distance $D_1$ across the channel 602, as measured in a direction at least substantially perpendicular to a major surface 606 of the litter 104 for supporting the mattress 200 (see FIG. 1) thereon, the major surface 606 facing the mattress 200 (see FIG. 1) when the mattress 200 (see FIG. 1) is supported thereon. The connector 416 of the second track 414 may also include, for example, alternating insertion valleys 608 spaced from one another by a second, greater distance $D_2$ across the channel 602. The teeth 604 may alternate with the insertion valleys 608, such that a tooth 604 may be interposed longitudinally between each pair of insertion valleys 608 and an insertion valley 608 may be interposed longitudinally between each pair of teeth 604. The teeth 604 and insertion valleys 608 may cooperatively define, for example, polygonal insertion points between adjacent teeth 604 to receive mating connectors 610 of the rings 700 (see FIG. 7), feet 418, and/or other modular accessories.

The mating connectors 610 may be sized and shaped to be inserted into the channel 602 when aligned with the insertion points and with the insertion valleys 608 and to be retained within the channel 602 when aligned with the teeth 604. For example, each mating connector 610 may include an enlarged head 612 at a distal end of the connector 610, the head 612 sized and shaped to pass through the insertion points proximate to the insertion valleys 608, but not to pass through the channel 602 when aligned with the teeth 604. For example, the head 612 of each mating connector 610 may have a diameter $D_3$ greater than the shortest first distance $D_1$ between adjacent teeth 604 across the channel 602 and less than the greatest second distance $D_2$ between adjacent insertion valleys 608 across the channel 602. Each mating connector 610 may further include a shaft 614 extending from the ring 700 (see FIG. 7), foot 418, and/or other modular accessory to the enlarged head 612. The shaft 614 of each connector 610 may have a smaller diameter $D_4$ than the diameter $D_3$ of the head 612 and smaller than the shortest first distance $D_1$ between adjacent teeth 604 across the channel 602.

The connector(s) 610 of the ring 700 (see FIG. 7), foot 418, and/or other modular accessory may be mated with the connector(s) 416 of the second track 414 by, for example, aligning each connector 610 with a corresponding insertion point and insertion valley 608, inserting the enlarged head 612 into the channel 602, and sliding the connector 610 longitudinally along the channel 602 to align each connector 610 with a corresponding tooth 604.

In some embodiments, one or more of the connectors 610 may include pins 618, hooks, loops, clamps, or threaded members configured to mate with corresponding holes 616, loops, hooks, ledges, or threaded holes 616 within the channel 602 to secure the connectors 610 in place. For example, the holes 616 may extend into a back wall of the channel 602 laterally inward from the teeth 604, and a spring-loaded pin 618 on the distal end of the head 612 may be biased to extend at least partially into the holes 616 when the pin 618 is aligned longitudinally with the hole 616 to maintain the head 612 aligned with mating teeth 604 and keep the connector 610 engaged with the second track 414 until the pin 618 is withdrawn from the hole 616. Such connectors 610 may be configured as, for example, quick-release connectors to enable quicker, easier connection to, and disconnection from, the litter 104.

In some embodiments, the first track 122 (see FIG. 1) and the associated connectors 124 may be configured at least substantially the same as described above for the second track 414 and associated connectors 610.

Figure 7:
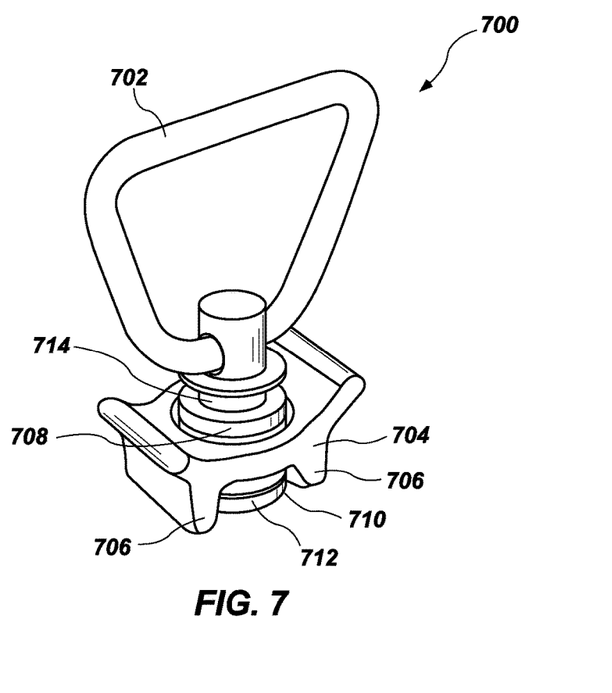
FIG. 7 is an enlarged perspective view of a ring of the interfacing mechanism of FIG. 4.

FIG. 7 is an enlarged perspective view of a ring 700 of the interfacing mechanism 402 of FIG. 4. In some embodiments, the ring 700 may include, for example, a connector 610 (e.g., a quick-release connector) as described previously in connection with FIG. 6. The ring 700 may further include a closed annular member 702 located proximate to a proximal end of the shaft 614 of the connector 610. The annular member 702 may be configured to receive the strap 404 of the interfacing mechanism 402 threaded (e.g., laced) therethrough.

In other embodiments, the ring 700 may include a quick-release connector 710 having a shaft 714 to which the annular member 702 is secured, an enlarged head 712 at an end of the shaft 714 opposite the annular member 702, and a housing 704 through which the shaft 714 may extend, such that the annular member 702 and the head 712 are located on opposite sides of the housing 704. The housing 704 may include protrusions 706 (which may also be characterized as "wings") extending longitudinally away from the annular member 702 and flanking the shaft 714 on two opposite lateral sides. A biasing element 708 (e.g., a coil spring, a leaf spring, a gas piston) may bias the head 712 toward a retracted position where the protrusions 706 are located adjacent to, and flank, the head 712, and permit the head 712 to move to an extended position where the head 712 is located beyond the protrusions 706.

With combined reference to FIGS. 6 and 7, the quick-release connector 710 of the ring 700 may be secured to the second track 414 (or to the first track 122 (see FIG. 1)) by aligning the head 712 with a given insertion valley 608 and aligning the protrusions 706 with the teeth 604 adjacent to the insertion valley 608. Force may be applied to the shaft 714 in a direction extending from the annular member 702 toward the head 712, urging the head 712 into the extended position beyond the teeth 604 and into the channel 602 as the shaft 714 moves relative to the housing 704, which may remain in place due to contact between the protrusions 706 and the teeth 604. The ring 700 may then be displaced laterally relative to the second track 414 (or to the first track 122 (see FIG. 1)), aligning the head 712 with one pair of teeth 604, which may reduce the likelihood that the head 712 may be removed from the channel 602 (e.g., may prevent removal). Lateral displacement of the ring 700 may also align the protrusions 706 with two adjacent insertion valleys 608, and the protrusions 706 may be moved into the insertion valleys 608, and the head 712 urged against the teeth 604, responsive to release of the force previously applied to the shaft 714. Mechanical interference between the teeth 604, the head 712, and the protrusions 706 may keep the ring 700 in place in a connector 416 of the second track 414 (or of the first track 122 (see FIG. 1)). The ring 700 may be removed from the connector 416 of the second track 414 (or of the first track 122 (see FIG. 1)) by reapplying the force to the shaft 714, pulling the housing 704 away from the channel 602 to remove the protrusions 706 from the insertion valleys 608, displacing the ring 700 laterally, and removing the head 712 from the channel via an aligned insertion valley 608.

Human stabilization platforms in accordance with this disclosure may enable a person to be more easily immobilized and transported while reducing risk of further injury due to undesirable movement of the person's body and undesirable contact between the human stabilization platform and injury sites. For example, head blocks and associated straps in accordance with this disclosure may be more difficult to dissociate from a remainder of the human stabilization platform, may be easier to put into position to immobilize a person's neck and head, and may be more secure when compared to conventional head blocks. As another example, restraint systems and associated interfacing mechanisms in accordance with this disclosure may enable more flexibility in positioning of associated straps, may enable more complete immobilization, reduce contact with injury sites, and permit fit adjustment without removing the restraint system. As yet another example, mattresses in accordance with this disclosure may enable easier transfer of a person supported thereon between litters while providing better support during such transfer.

While certain illustrative embodiments have been described in connection with the figures, those of ordinary skill in the art will recognize and appreciate that the scope of this disclosure is not limited to those embodiments explicitly shown and described in this disclosure. Rather, many additions, deletions, and modifications to the embodiments described in this disclosure may be made to produce embodiments within the scope of this disclosure, such as those specifically claimed, including legal equivalents. In addition, features from one disclosed embodiment may be combined with features of another disclosed embodiment while still being within the scope of this disclosure.

What is claimed is:

1. A restraint system for stabilizing a human, comprising:
an interfacing mechanism for securing a portion of a restraint to a litter, the restraint comprising a plurality of straps, straps of the plurality of straps comprising a set of conduits extending along, and secured to, a lateral side of the restraint, the interfacing mechanism comprising:
a set of releasable connectors configured to selectively secure portions of the interfacing mechanism to corresponding attachment points distributed along a lateral side of the litter, each releasable connector of the set of releasable connectors comprising a respective ring; and
a strap threadable through the respective ring of each releasable connector of the set of releasable connectors and through the conduits of respective straps of the restraint, the strap being adjustable in length to adjust a fit of the restraint system.

2. The restraint system of claim 1, further comprising the restraint for positioning at least partially over a torso of a human, the restraint comprising other straps for positioning over corresponding portions of the torso of the human and for interlacing with the strap of the interfacing mechanism for securing the restraint to the litter.

3. The restraint system of claim 2, wherein the restraint comprises a lattice-style restraint.

4. The restraint system of claim 1, further comprising:
a second interfacing mechanism for securing another, different portion of the restraint on an opposite side of the restraint to the litter, the second interfacing mechanism comprising:
  a second set of releasable connectors configured to selectively secure portions of the restraint to corresponding attachment points distributed along another, opposite lateral side of the litter; and
  a second strap threadable through each releasable connector of the second set of releasable connectors and through respective straps of the restraint, the second strap being adjustable in length to adjust the fit of the restraint system.

5. The restraint system of claim 1, further comprising the litter configured to support a human on or above the litter, the litter comprising a track extending along a lateral side of the litter, the track comprising the attachment points configured to receive the releasable connectors of the set of releasable connectors to secure the interfacing mechanism to the litter.

6. The restraint system of claim 5, wherein the track of the litter comprises a channel comprising alternating teeth spaced from one another by a distance across the channel.

7. The restraint system of claim 1, wherein the set of conduits comprises tubular sections of resilient material.

8. The restraint system of claim 1, wherein the set of conduits alternates with the releasable connectors of the set of releasable connectors along a length of the interfacing mechanism, such that a conduit is located longitudinally between each pair of releasable connectors of the first set of releasable connectors and a releasable connector of the first set of releasable connectors is located longitudinally between each pair of conduits.

9. The restraint system of claim 1, wherein each releasable connector of the set of releasable connectors comprises a quick-release connector configured to selectively engage with the litter.

10. The restraint system of claim 1, wherein each releasable connector of the set of releasable connectors comprises:
  a shaft extending through a housing, wherein the housing comprises protrusions located adjacent to the shaft on two opposite lateral sides of the shaft;
  the respective ring comprising an annular member located at a first end of the shaft;
  a head located at a second end of the shaft; and
  a biasing element biasing the head toward a retracted position in which the protrusions are located adjacent to the head, the head movable relative to the housing to an extended position in which the head extends beyond the protrusions.

11. The restraint system of claim 1, further comprising a selectable buckle proximate to a distal end of the strap, the selectable buckle configured to selectively release the strap to adjust the length of the strap through the buckle and to selectively fix the strap in place to inhibit changing the length of the strap.

12. A restraint system for stabilizing a human, comprising:
  a first interfacing mechanism for securing a portion of a restraint to a litter, the restraint comprising a plurality of straps, straps of the plurality of straps comprising first and second sets of conduits extending along, and secured to, respective lateral sides of the restraint, the first interfacing mechanism comprising:
    a first set of releasable connectors configured to selectively secure portions of the first interfacing mechanism to corresponding attachment points distributed along a lateral side of the litter, each releasable connector of the first set of releasable connectors comprising a respective first ring; and
    a first strap threadable through the respective first ring of each releasable connector of the first set of releasable connectors and through conduits of the first set of conduits of respective straps of the restraint, the first strap being adjustable in length to adjust a fit of the restraint system; and
  a second interfacing mechanism for securing a second, different portion on an opposite side of the restraint to the litter, the second interfacing mechanism comprising:
    a second set of releasable connectors configured to selectively secure portions of the second interfacing mechanism to a corresponding attachment points distributed along another, opposite lateral side of the litter, each releasable connector of the second set of releasable connectors comprising a respective second ring; and
    a second strap threadable through the respective second ring of each releasable connector of the second set of releasable connectors and through conduits of the second set of conduits of respective straps of the restraint, the second strap being adjustable in length to adjust a fit of the restraint system.

13. The restraint system of claim 12, further comprising the restraint for positioning at least partially over a torso of a human, the restraint comprising other straps for positioning over corresponding portions of the torso of the human and for interlacing with the first and second straps of the first and second interfacing mechanisms for securing the restraint to the litter.

14. The restraint system of claim 12, further comprising the litter configured to support a human on or above the litter, the litter comprising a track extending along a lateral side of the litter, the track comprising the attachment points configured to receive the releasable connectors of the first and second sets of releasable connectors to secure the interfacing mechanism to the litter.

15. The restraint system of claim 12, wherein the first and second sets of conduits comprise tubular sections of resilient material.

16. The restraint system of claim 12, wherein the first and second sets of conduits alternate with the releasable connectors of the first and second sets of releasable connectors along lengths of the first and second interfacing mechanisms, respectively, such that a conduit is located longitudinally between each pair of releasable connectors and a releasable connector is located longitudinally between each pair of conduits.

17. The restraint system of claim 12, wherein each releasable connector of the first and second sets of releasable connectors comprises a quick-release connector configured to selectively engage with the litter.

18. The restraint system of claim 12, wherein each releasable connector of the first and second sets of releasable connectors comprises:
  a shaft extending through a housing, wherein the housing comprises protrusions located adjacent to the shaft on two opposite lateral sides of the shaft;
  the respective first or second ring comprising an annular member located at a first end of the shaft;
  a head located at a second end of the shaft, on two opposite lateral sides of the shaft; and a biasing element biasing the head toward a retracted position in which the protrusions are located adjacent to the head, the head movable relative to the housing to an extended position in which the head extends beyond the protrusions.

* * * * *